United States Patent
Crothall et al.

(10) Patent No.: US 7,179,226 B2
(45) Date of Patent: Feb. 20, 2007

(54) SYSTEM AND METHOD FOR MANAGING DIABETES

(75) Inventors: Katherine D. Crothall, Haverford, PA (US); Bogdan Butoi-Teodorescu, Devon, PA (US); Peter Laakmann, Haverford, PA (US)

(73) Assignee: Animas Corporation, West Chester, PA (US)

( * ) Notice: Subject to any disclaimer, the term of this patent is extended or adjusted under 35 U.S.C. 154(b) by 221 days.

(21) Appl. No.: 10/176,390

(22) Filed: Jun. 19, 2002

(65) Prior Publication Data

US 2003/0032867 A1 Feb. 13, 2003

Related U.S. Application Data

(60) Provisional application No. 60/299,802, filed on Jun. 21, 2001.

(51) Int. Cl.
 *A61B 5/00* (2006.01)
(52) U.S. Cl. ........................ 600/300; 128/920
(58) Field of Classification Search ........ 600/300–301, 600/345–347, 365, 309, 316; 128/904, 920, 128/925, 923; 435/265, 232, 118; 607/64–67; 707/9; 702/19
See application file for complete search history.

(56) References Cited

U.S. PATENT DOCUMENTS

| | | | |
|---|---|---|---|
| 4,891,756 A | 1/1990 | Williams, III | |
| 5,732,709 A * | 3/1998 | Tacklind et al. | 600/539 |
| 5,997,475 A | 12/1999 | Bortz | |
| 6,188,648 B1 | 2/2001 | Olsen | |
| 6,234,964 B1 | 5/2001 | Iliff | |
| 6,277,071 B1 | 8/2001 | Hennessy et al. | |
| 6,278,999 B1 | 8/2001 | Knapp | |
| 6,352,505 B1 | 3/2002 | Bortz | |
| 6,368,272 B1 * | 4/2002 | Porumbescu | 600/300 |
| 6,513,532 B2 * | 2/2003 | Mault et al. | 600/595 |

\* cited by examiner

*Primary Examiner*—Max F. Hindenburg
*Assistant Examiner*—Michael C Astorino
(74) *Attorney, Agent, or Firm*—RatnerPrestia

(57) ABSTRACT

A diabetes management system and method used to manage the blood glucose level of a diabetes patient. The system includes at least one portable electronic device and a database system. The portable electronic device allows the patient to input different types of data into the processor to calculate insulin and carbohydrate intake recommendations for the patient. A time/date stamp is individually generated and stored for each type of data inputted by the patient. The diabetes management system also includes a database system which stores (i) activity data associated with the physical activity of the patient, (ii) blood glucose data associated with the blood glucose level of the patient, (iii) meal intake data associated with the food intake of the patient, and (iv) insulin intake data associated with the insulin intake of the patient.

23 Claims, 17 Drawing Sheets

SYSTEM AND METHOD FOR MANAGING DIABETES

CROSS-REFERENCE TO RELATED APPLICATION

This application claims the benefit of U.S. Provisional Application No. 60/299,802, filed Jun. 21, 2001, entitled "Method and Apparatus for Managing Diabetes," which is incorporated herein by reference in its entirety.

BACKGROUND OF THE INVENTION

The present invention relates to a system and method for managing diabetes. More particularly, the present invention is related to a diabetes management application for use with handheld organizers.

A number of diabetes management programs for handheld devices currently exist. However, these devices exhibit limited functionality and are often difficult to use. The existing diabetes management software packages that are capable of handling a plurality of logs for blood glucose levels, insulin shots, meals, activities, etc., are designed in such a way that the information is held in one record. By storing information in one record, the user is affected in a number of ways including: harder to read logs, one date/time stamp for actions which may occur 30 or more minutes apart, and a database occupying significant amount of space. Additionally, storing information in one record and, for example, entering only blood glucose information at a particular point, results in poor space allocation for meal information, insulin dosage information or activity data. Consequently, space allocated in a particular database record for specific values will be lost.

What is needed is a diabetes management system and method that stores each type of data used to manage the blood glucose level of a diabetes patient in individual time/date stamped records that can be stored in a database system for future review by a health professional.

BRIEF SUMMARY OF THE INVENTION

The present invention is a system and computer-implemented method which manage the blood glucose level of a diabetes patient. A data input interface is provided which allows the patient to input different types of data used to calculate at least one of insulin and carbohydrate intake recommendations for the patient. The types of inputted data include (i) activity data associated with the physical activity of the patient, (ii) blood glucose data associated with the blood glucose level of the patient, (iii) meal intake data associated with the food intake of the patient, and (iv) insulin intake data associated with the insulin intake of the patient. A time/date stamp is individually generated for each type of data inputted by the patient. The data inputted by the patient and the respective time/date stamp is stored in a database.

An external database may be accessed to retrieve supplemental information, associated with at least one of the activity data and the meal intake data, to calculate at least one of the insulin and carbohydrate intake recommendations for the patient. The external database may be a food database which provides extended search capabilities. The patient may select, via the data interface, one or more food items from the food database. Portion size data associated with each food item may be adjusted so that the portion size corresponds to the amount ingested by the patient. The total nutritional content of a meal ingested by the patient may be calculated based on the selected food items and portion size data. The external database may be a food database which includes at least part of the USDA food database. The food database may include foods offered from at least one national or regional chain restaurant.

The blood glucose data may be received from a blood glucose meter which monitors the blood of the patient. The insulin intake data may be received from an insulin pump which distributes insulin intake into the blood of the patient. Insulin intake recommendations may be based on the food intake data. The food intake data may include at least one of carbohydrate intake data, fat intake data and protein intake data. Multiple insulin to carbohydrate compensation ratios may be stored based on a time and/or meal type deemed appropriate for the patient. The activity data may include calories burned by the patient during an activity. The carbohydrate intake recommendations may be based on the activity data.

In accordance with one embodiment of the present invention, a diabetes management system for managing the blood glucose level of a diabetes patient including at least one portable electronic device with a data input interface and a processor, and a database system in communication with the processor. The data input interface allows the patient to input different types of data into the processor to calculate insulin and carbohydrate intake recommendations for the patient.

In another embodiment of the present invention, a diabetes management system for managing the blood glucose level of a diabetes patient includes an insulin pump with a processor which monitors the insulin intake of the patient, and a database system in communication with the processor of the insulin pump. The database system stores insulin intake data associated with the insulin intake of the patient. A time/date stamp is individually generated and stored with the insulin intake data.

In yet another embodiment of the present invention, a diabetes management system for managing the blood glucose level of a diabetes patient includes a blood glucose meter including a processor which monitors the blood glucose level of the patient, and a database system in communication with the processor of the blood glucose meter. The database system stores blood glucose level data associated with the blood glucose level of the patient. A time/date stamp is individually generated and stored with the blood glucose data.

BRIEF DESCRIPTION OF THE SEVERAL VIEWS OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

The present invention comprises a system and method for management of diabetes. A preferred embodiment of the present invention includes a diabetes management application designed for operation on a handheld organizer, such as a Palm OS device. The present invention is used to log blood glucose levels, insulin intake, and nutrition information (carbohydrates, protein, fiber, fat and calories), activity and notes. Based on user settings such as carbohydrates to insulin ratios for various kinds of meals, protein, fat and fiber compensation, blood glucose target area, high/low glucose levels compensation through insulin and carbohydrates, and weight, the present invention computes the recommended dosage taking into consideration variables such as blood glucose level, activity, meals, etc.

A preferred embodiment of the invention is designed for operating on the Palm OS platform. The database structure and search capabilities preferably incorporate the use of the Palm OS API to provide sufficient speed and reliability.

The present invention preferably uses one or more reference databases for computing meal nutrition factors and/or the amount of calories burned during activities. A food database is preferably provided for use with a handheld device. The food database preferably comprises at least a portion of the USDA food nutrition facts database 130. The food database preferably includes the most used items from the USDA food nutrition facts database. A corresponding desktop application is also provided which preferably contains corresponding portions of the USDA food nutrition facts database which can be uploaded as needed to the handheld device.

In one embodiment of the present invention, the total amount of carbohydrates, protein and fats contained in a meal is preferably computed by the handheld device or the desktop application based on the selected items and quantities entered by a user. A recommended insulin dosage which compensates for a particular meal is provided using user set carbohydrate to insulin ratios and rules for protein, fat and fiber.

The present invention further preferably incorporates an activity database which contains a list of common sports activities and the calorie burn ratios per minute per pound of body weight. Based on a user's entered weight and duration of activity, the present invention preferably computes the amount of calories burned and recommends an amount of carbohydrates needed to compensate for the burned calories.

The present invention is preferably capable of synchronizing databases between a handheld device and a personal computer running the desktop application.

Figure 1:
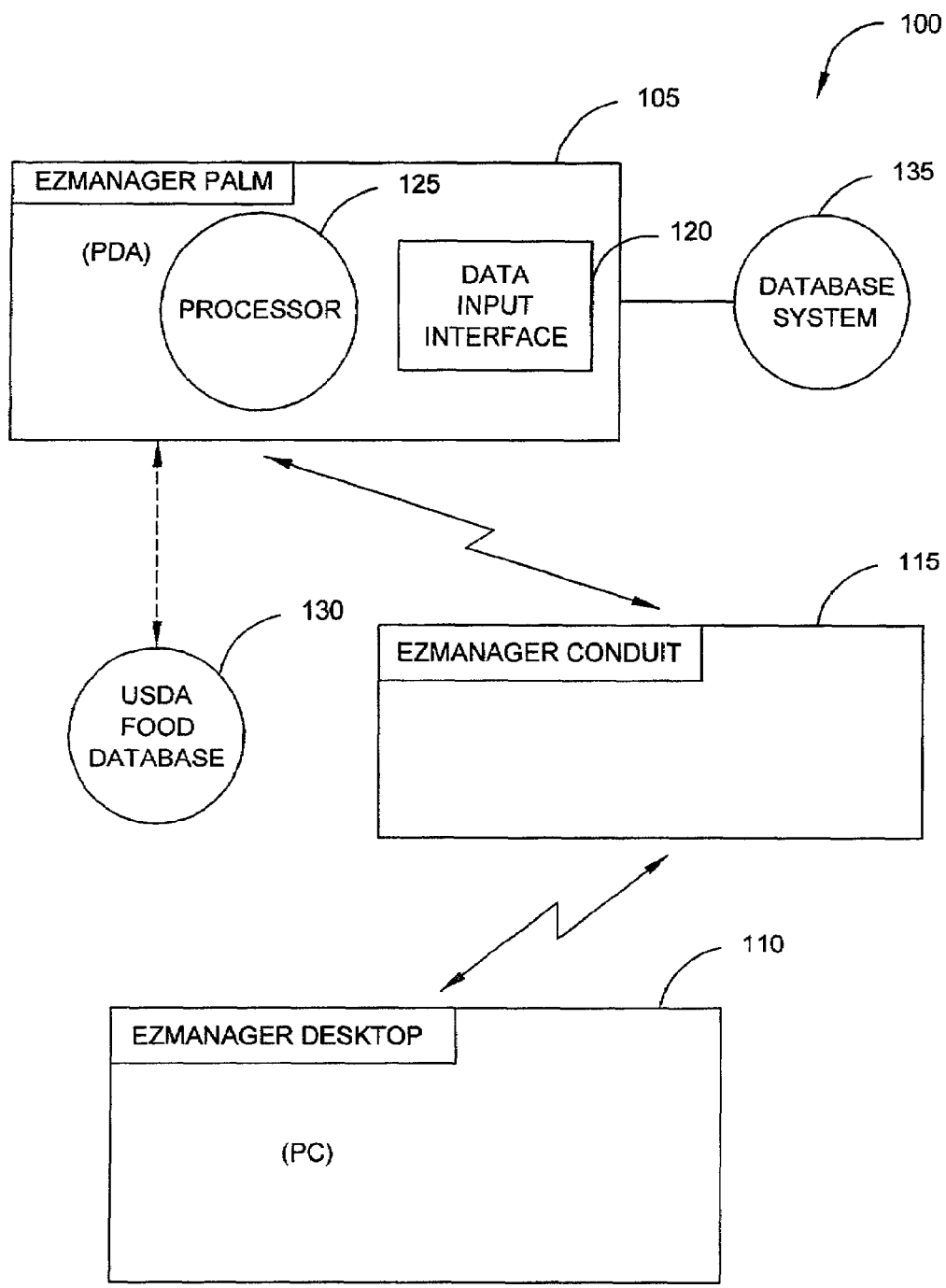
FIG. 1 shows a block diagram of a diabetes management system in accordance with the present invention.

FIG. 1 shows a diabetes management system 100 in accordance with a preferred embodiment of the present invention. The diabetes management system 100 includes at least one Personal Digital Assistant (PDA) 105 (also referred to as ezManager Palm), a personal computer (PC) 110 (also referred to as ezManager Desktop) and a conduit 115 (also referred to as ezManager Conduit) which is in communication with the PDA 105 and PC 110. Conduit 115 synchronizes data between PDA 105 and PC 110. This process is known as HotSync. An operating system (OS) runs on the PC 110, such as Palm OS v3.0 or higher. An OS also runs on PC 110, such as Windows 9x/ME/2000/XP. The diabetes management system 100 manages the blood glucose level of a diabetes patient and includes at least one portable electronic device (PDA 105) including a data input interface 120 and a processor 125. The data input interface allows the patient to input different types of data into the processor 125 to calculate insulin and carbohydrate intake recommendations for the patient. The diabetes management system 100 also includes a database system in communication with the processor 125. The database system 135 stores different types of the data inputted by the patient, including (i) activity data associated with the physical activity of the patient, (ii) blood glucose data associated with the blood glucose level of the patient, (iii) meal intake data associated with the food intake of the patient, and (iv) insulin intake data associated with the insulin intake of the patient. A time/date stamp is individually generated and stored for each type of data inputted by the patient.

The PDA 105 is also known as a hand held (HH) device and has an internal database (DB) which may store up to six months of data in less than 512K of memory. The PDA 105 synchronizes with the PC 110 via conduit 115 to archive data and create reports. The conduit 115 contains a set of rules on which synchronization between PDA 105 and PC 110 is based. The PDA 105 is used to log physical activity, blood glucose (BG), insulin intake, meals, and notes of a diabetes patient who uses the diabetes management system 100. The PDA 105 computes and recommends amounts of carbohydrates and insulin that the diabetes patient should consume based on types of data inputted by the diabetes patient via a user interface (UI) presented by the PDA 105. The PDA 105 also computes the hyperglycemia or hypoglycemia compensation based on input by the diabetes patient. The PDA 105 is used to log physical activity, blood glucose (BG), insulin intake, meals, and notes of a diabetes patient who uses the diabetes management system 100. The PC 110 is used to log physical activity, blood glucose (BG), insulin intake, meals, and notes from one or more diabetes patients using one or more PDAs 105.

Figure 2:
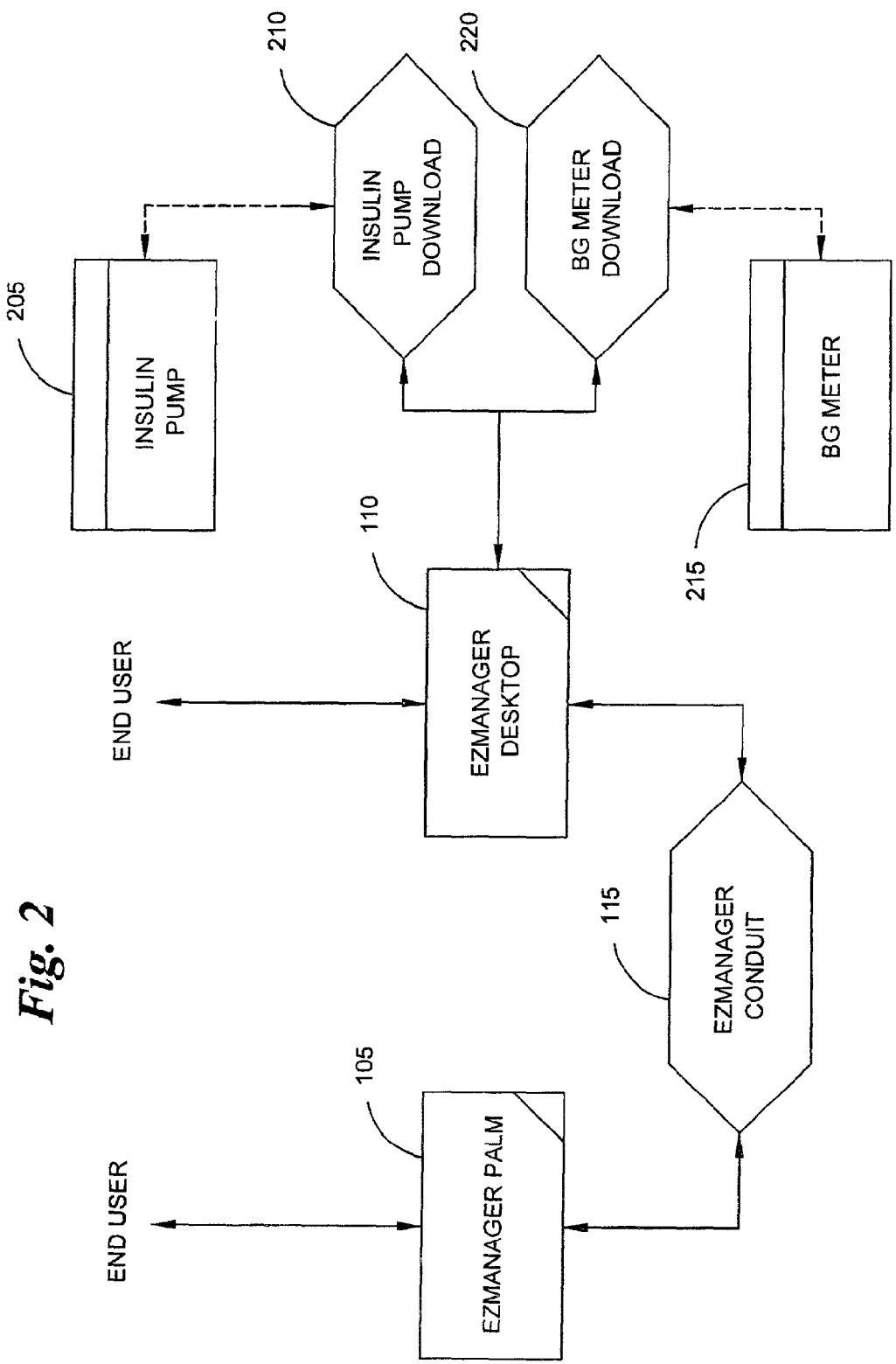
FIG. 2 shows the diabetes management system of FIG. 1 interfacing with an insulin pump and blood glucose meter in accordance with the present invention.
Figure 3A:
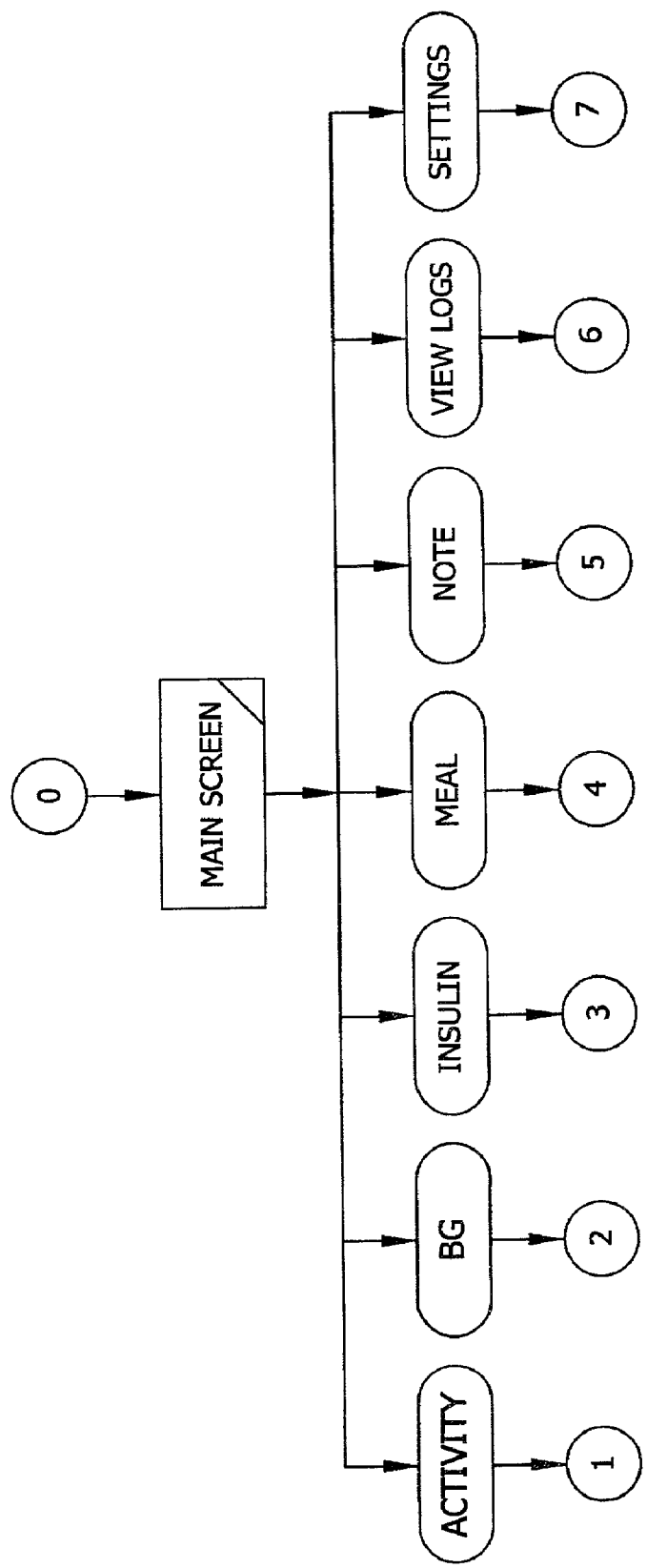
FIGS. 3–8 show flow charts of how the database and log structures operate in accordance with the present invention.
Figure 3B:
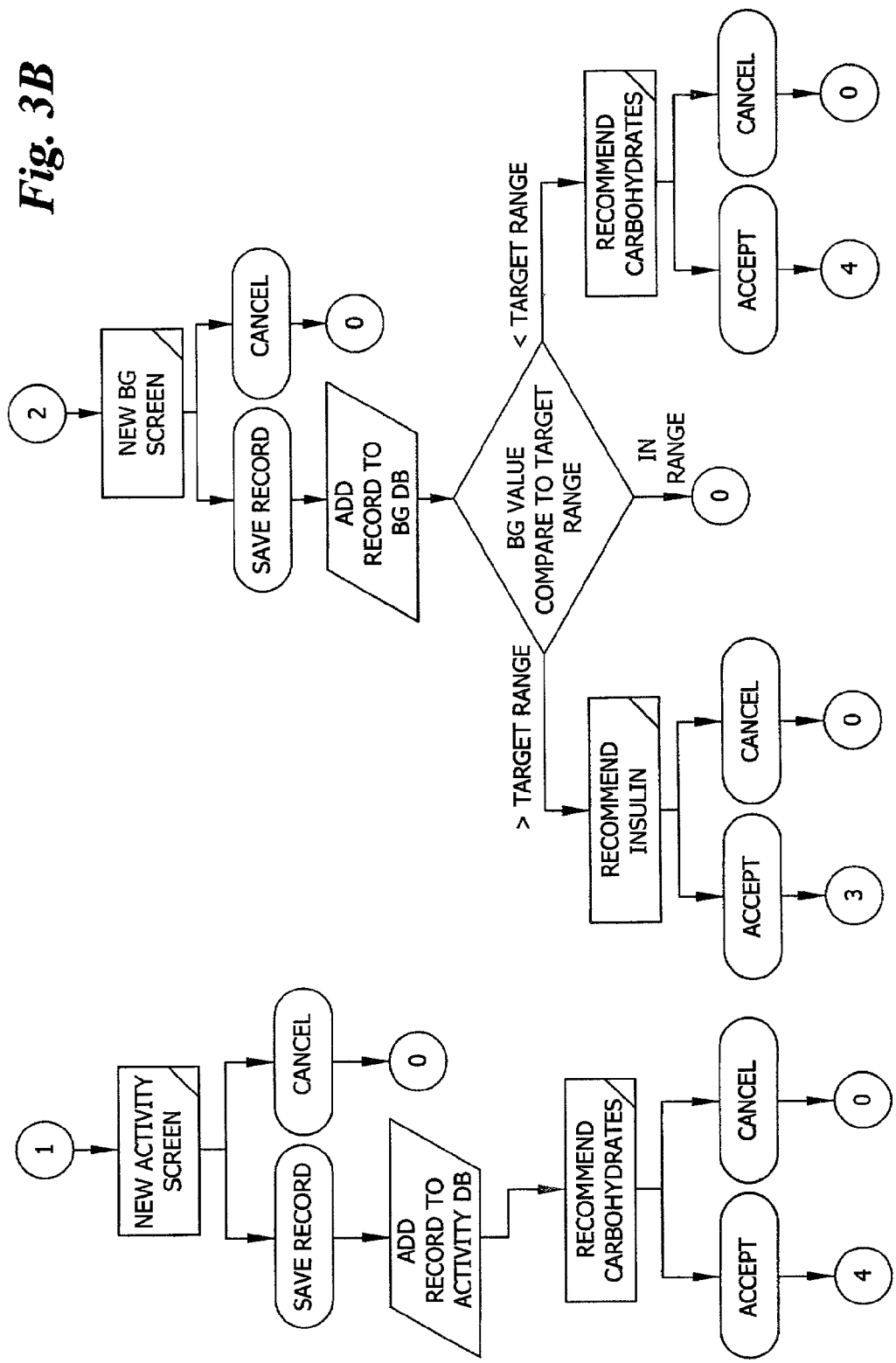
Figure 3C:
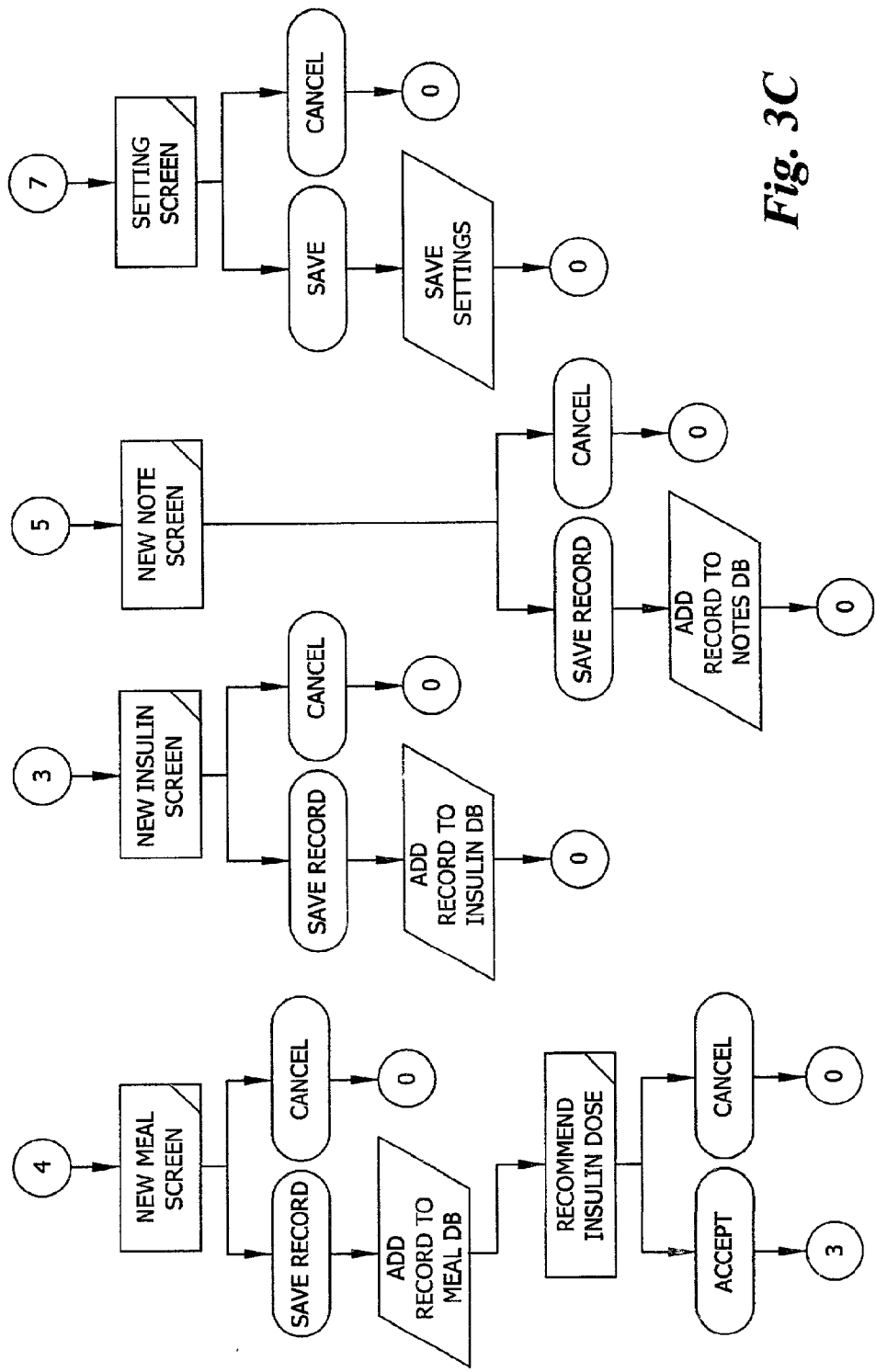
Figure 3D:
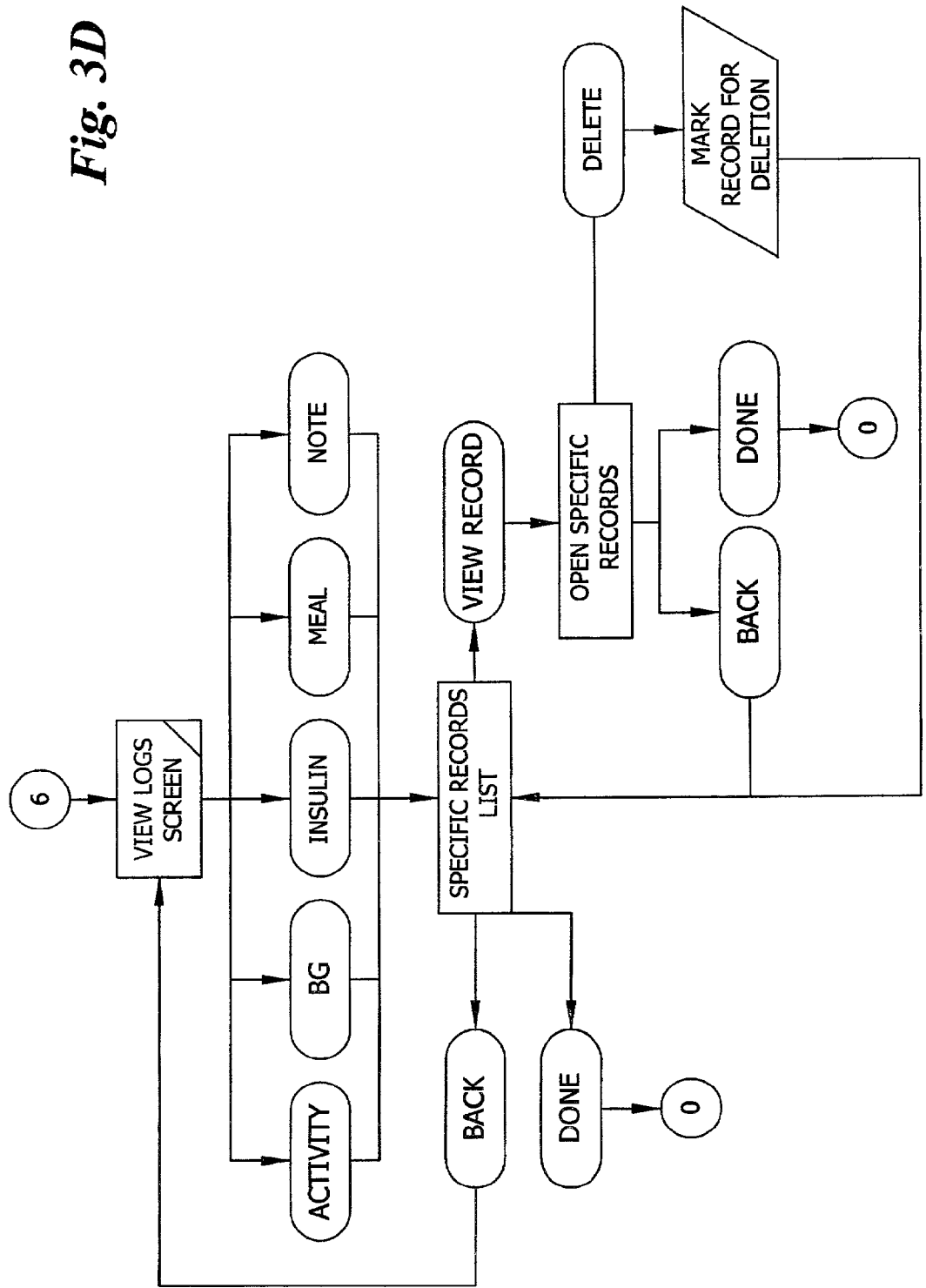
Figure 4A:
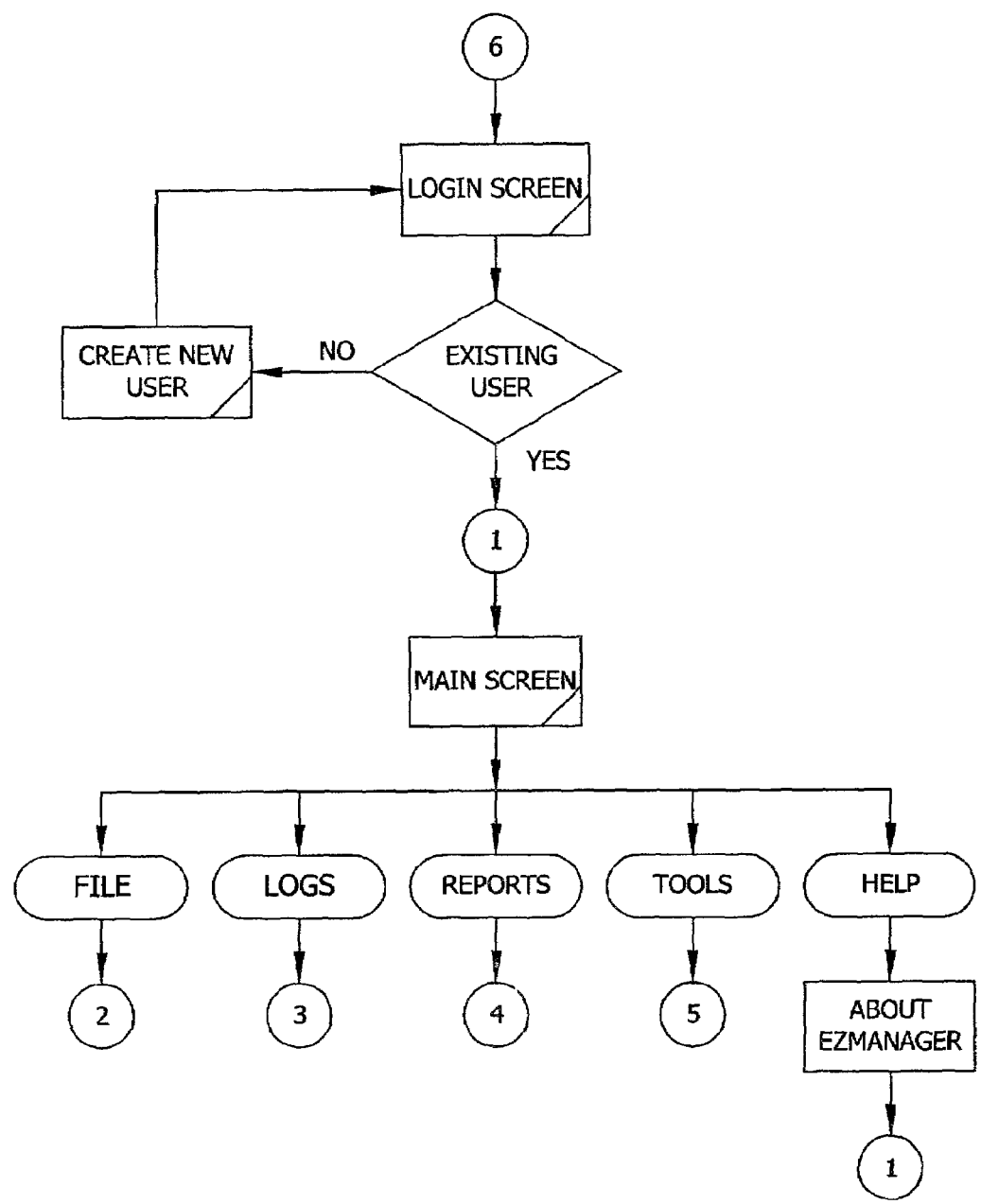
Figure 4B:
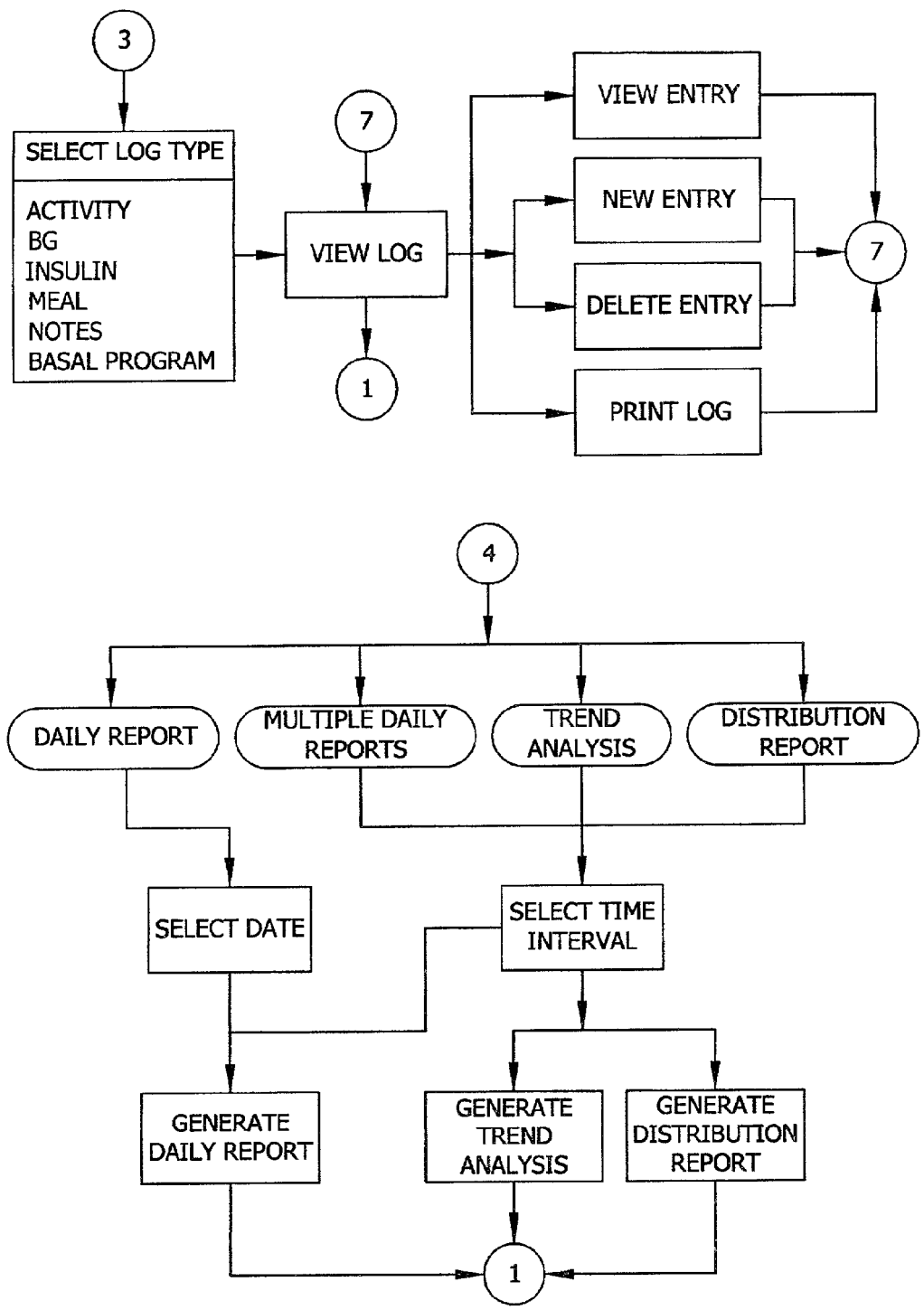
Figure 4C:
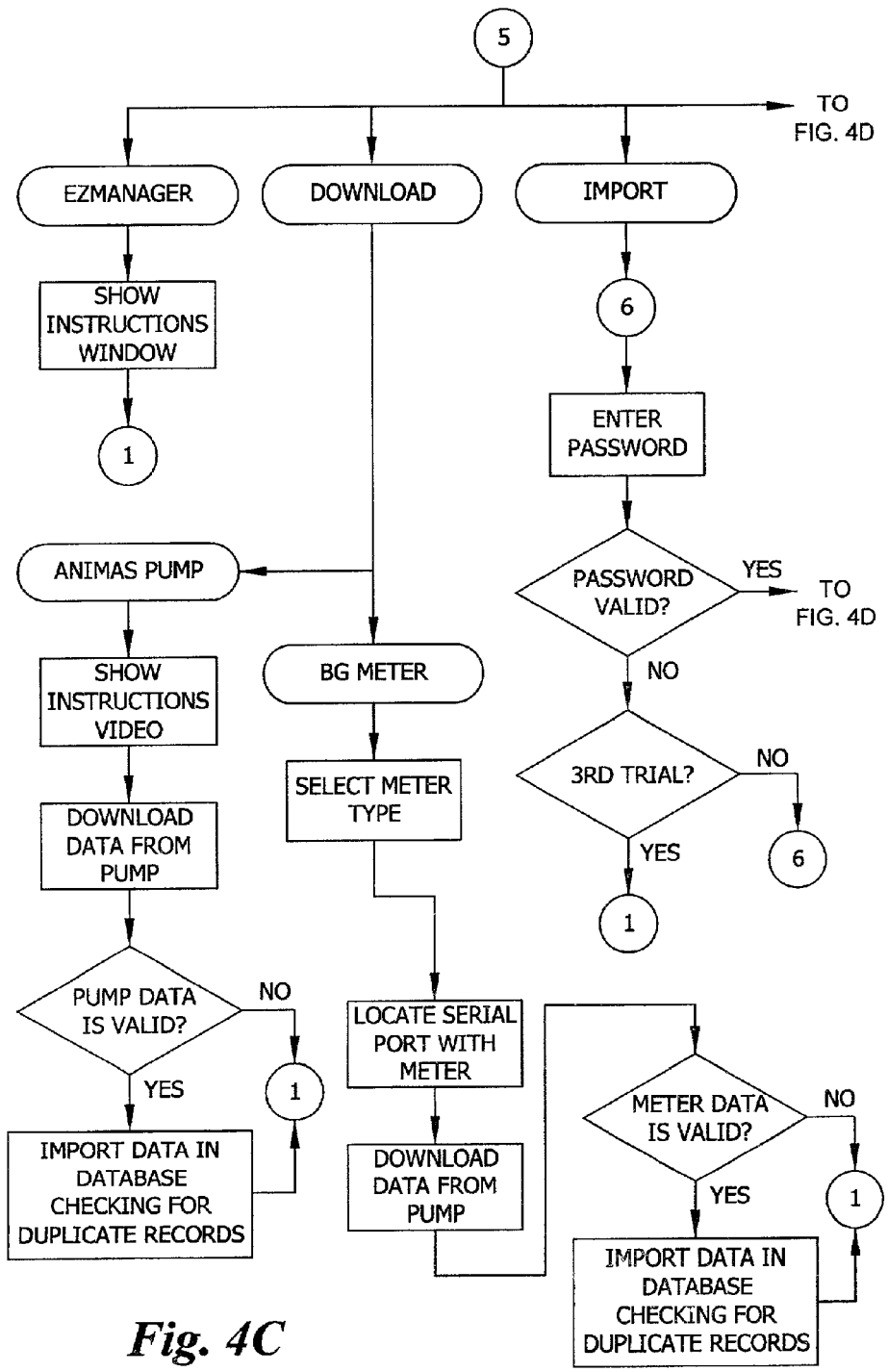
Figure 4D:
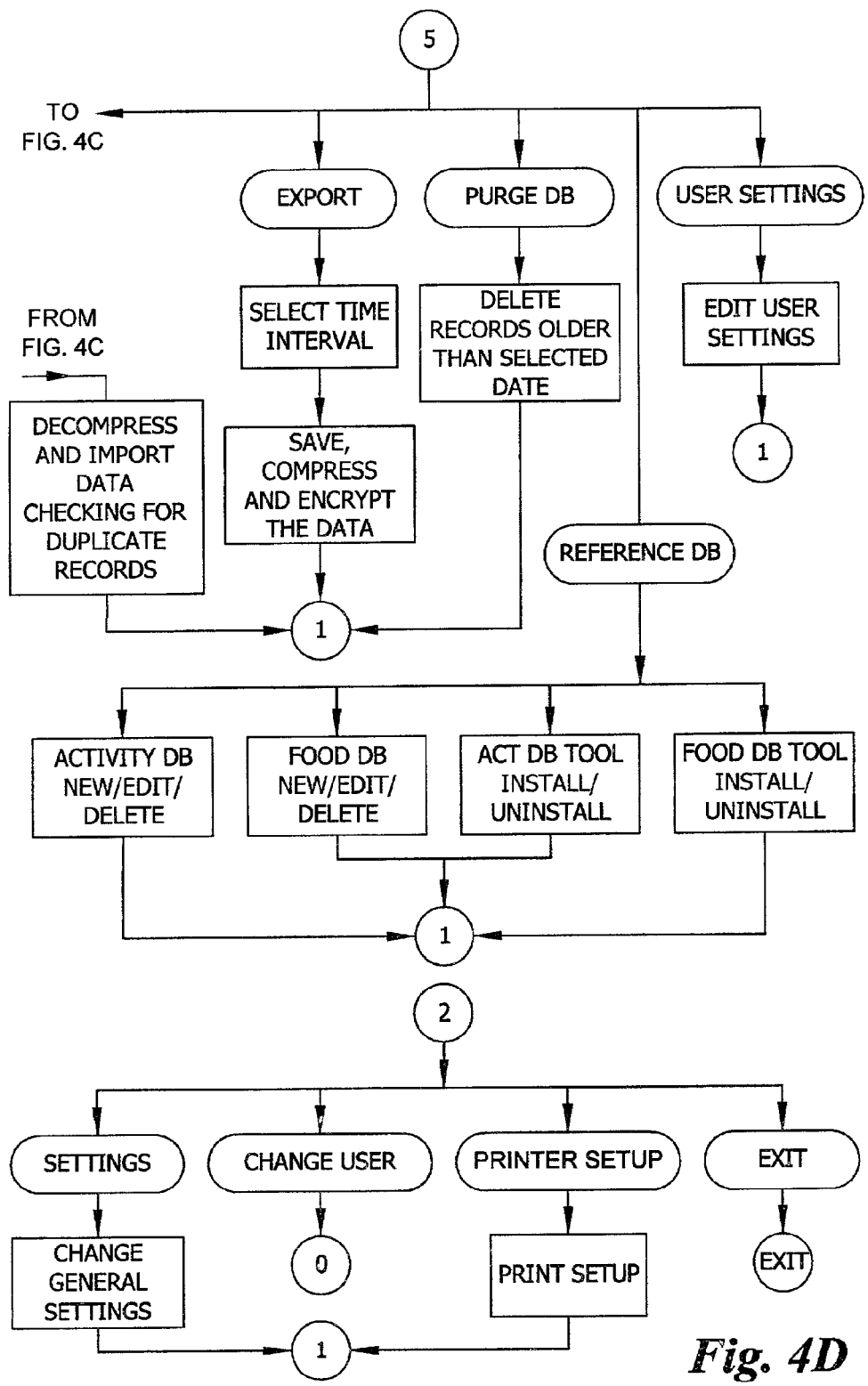
Figure 5:
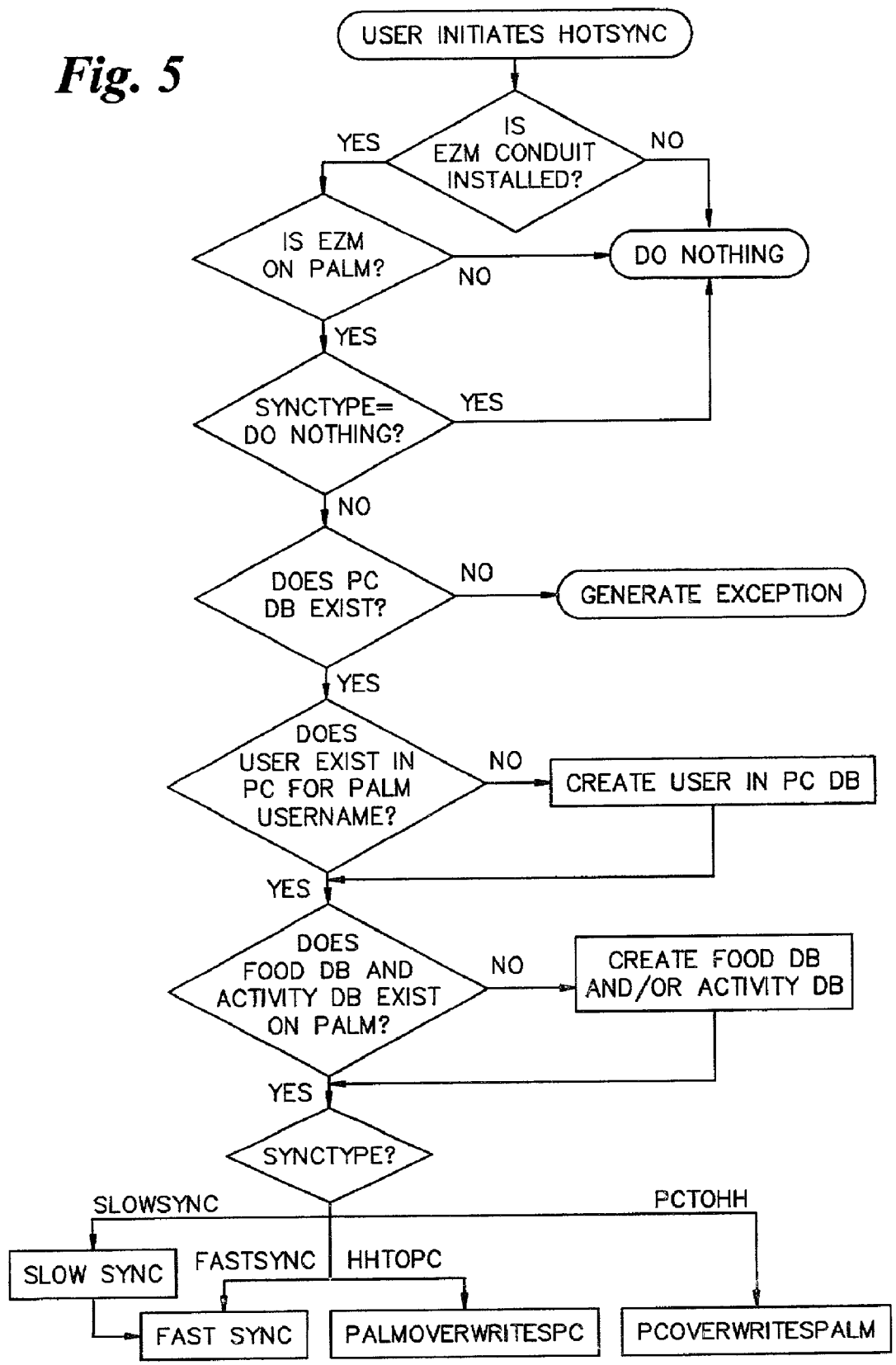
Figure 6A:
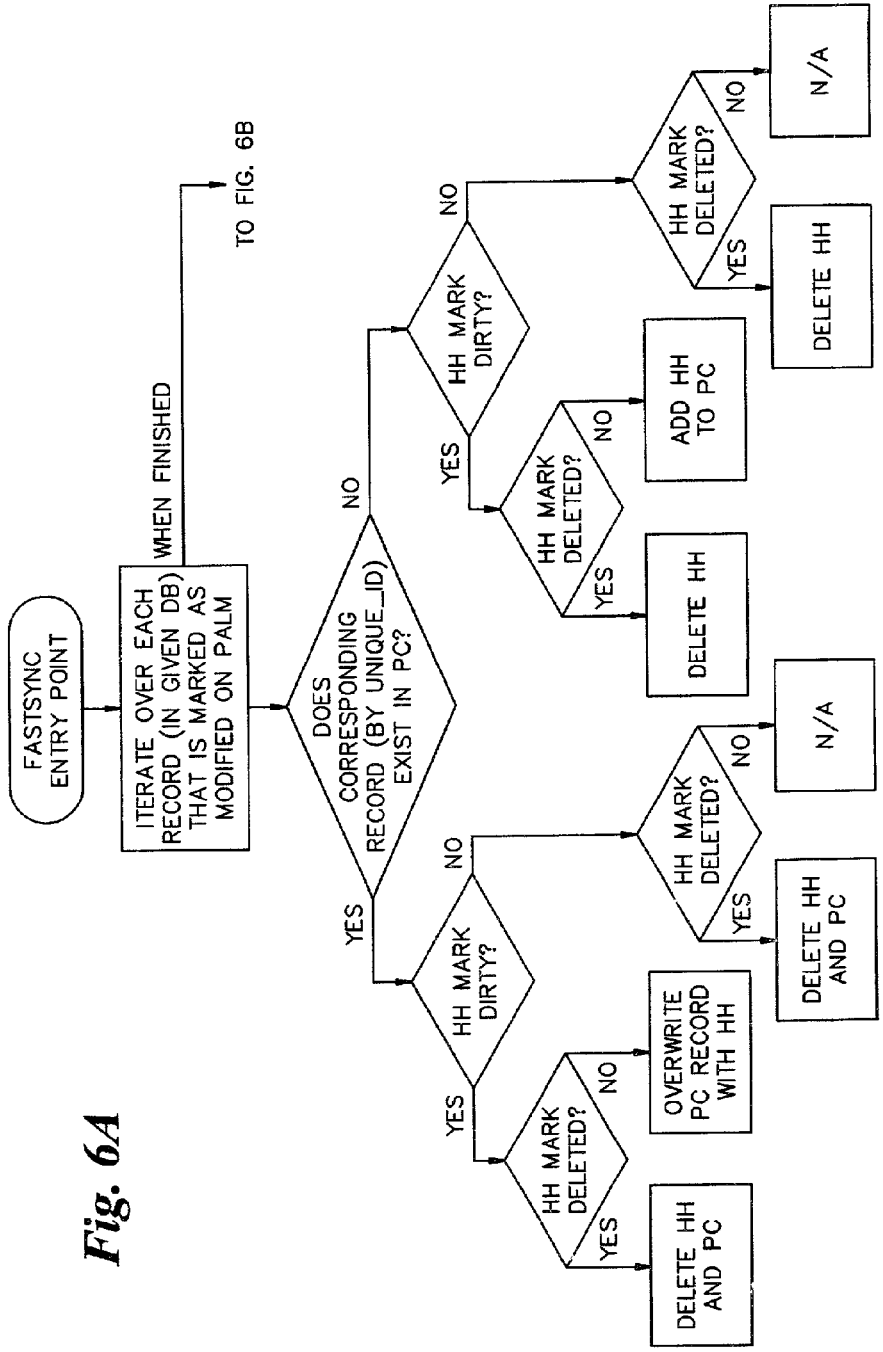
Figure 6B:
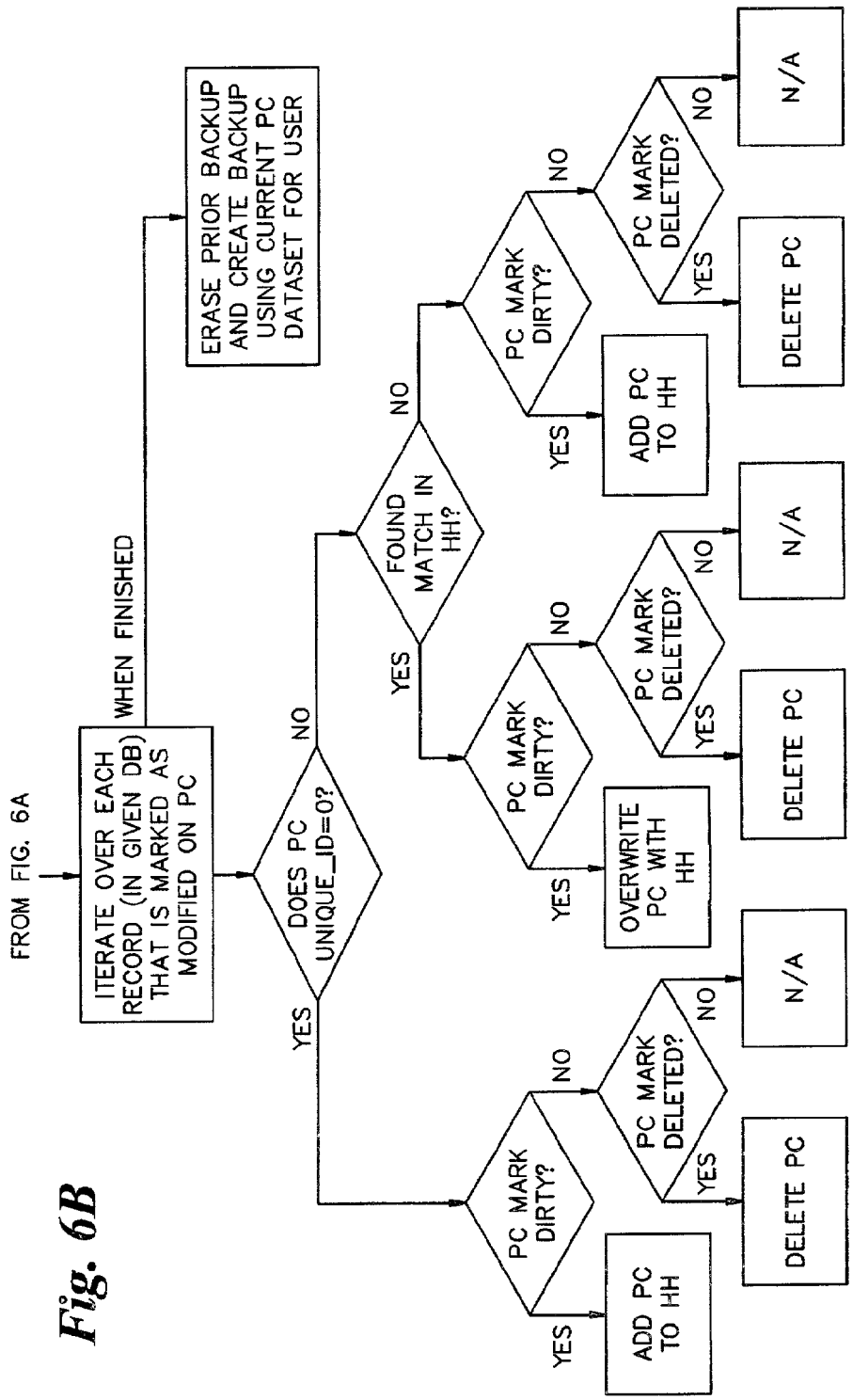
Figure 7:
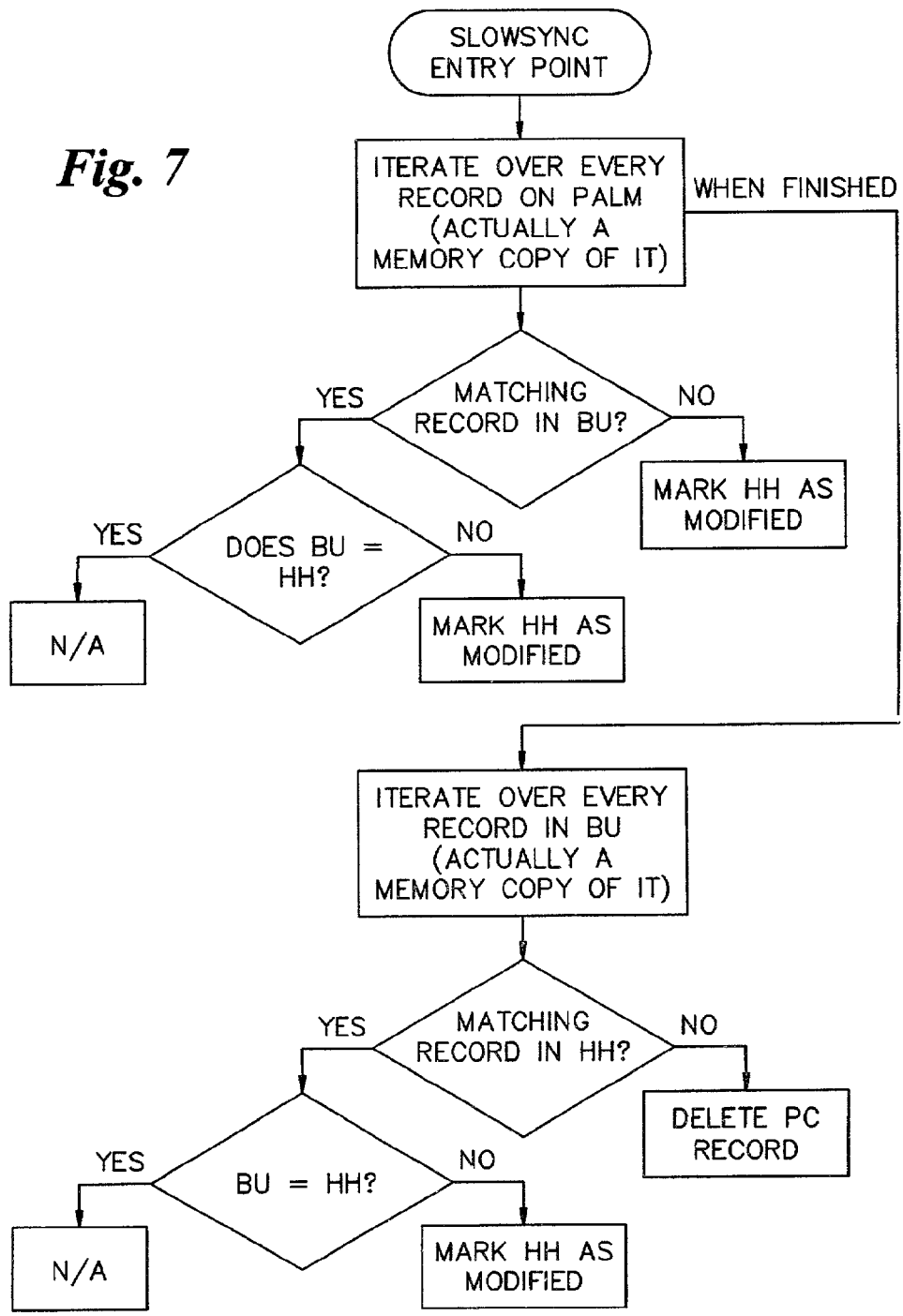
Figure 8:
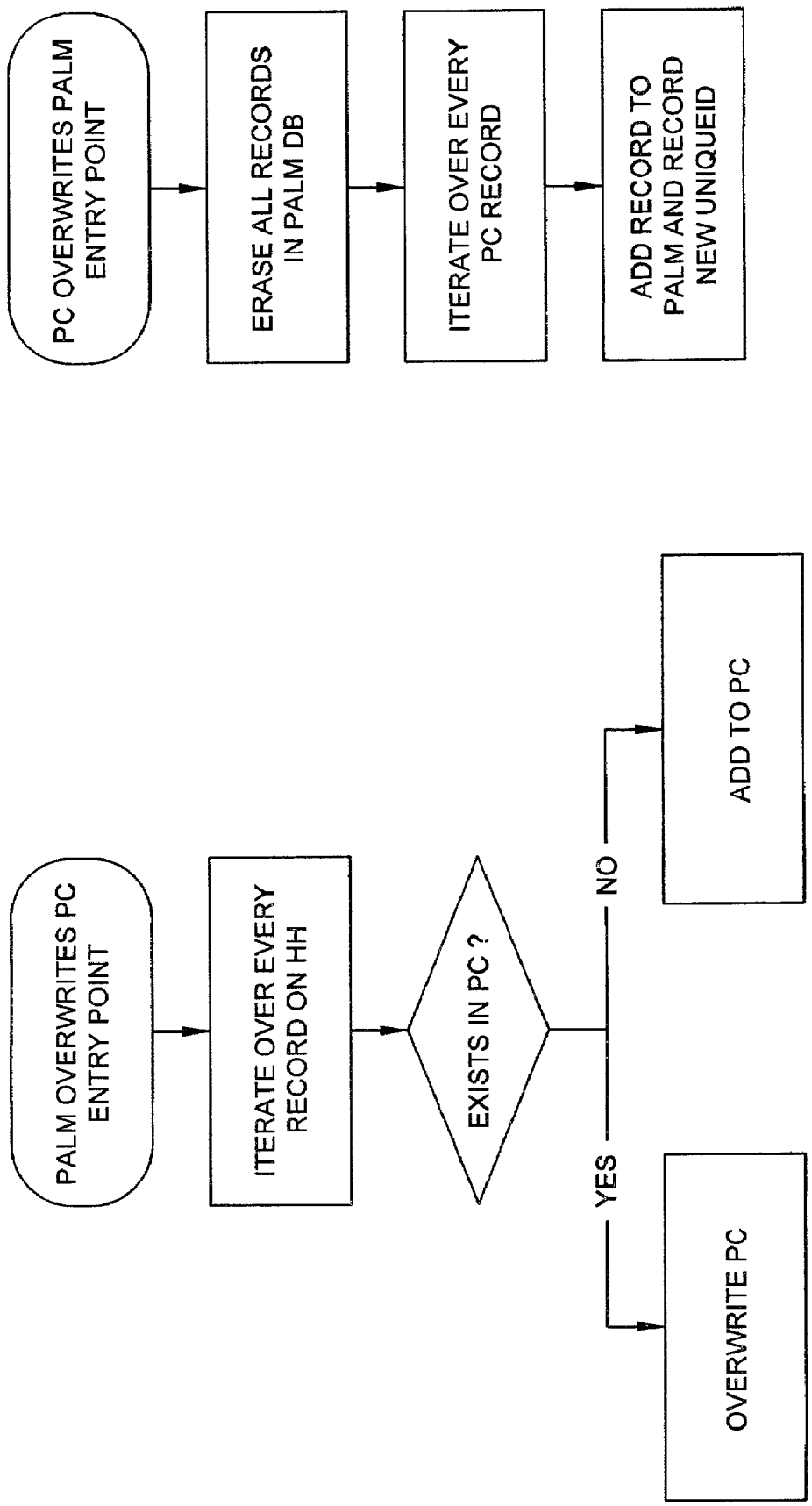

As shown in FIG. 2, PC 110 may also be linked with one or more blood glucose (BG) meters 215 and/or insulin pumps 205 which download insulin pump data 210 and BG meter data 220 to the PC 110. PC 110 can create reports based on the data which is stored in a database. Multiple user's records may be kept separately in individual files associated with different diabetes patients. PC 110 may use a Microsoft Access data base format which operates in conjunction with conduit 115 to synchronize with the PDA 105 to upload/download logs and Activity and Food databases.

The diabetes management system 100 computes and recommends amounts of carbohydrates and insulin that the diabetes patient should consume based on types of data inputted by the diabetes patient via a user interface (UI) presented by the PDA 105.

In one preferred embodiment of the present invention, a desktop application is provided as a counterpart to an application running on a handheld device. The desktop application preferably contains all of the functionalities of the handheld application along with extended reporting and database maintenance capabilities. The desktop application preferably uses an MS Access database structure and ActiveX data objects database connections. Preferably, the synchronization dynamic library is compliant with the Palm OS Conduit requirement.

The present invention is preferably also designed to provide for ready integration with insulin pumps using, for example, an infrared link. Preferably, the present invention can download and centralize information regarding insulin boluses, daily totals history, alarm history—with a description for each code, actual settings and programs, and the like. The present invention preferably also can download information from any number of glucometer devices. The present invention also preferably provides easy data entry for users, allowing a user to focus on recording of meals, activities and important events.

Preferably, data can be downloaded from the handheld device to one or more databases operating in connection with the desktop application. A user preferably is able to analyze data downloaded to the desktop application using a number of tabular listings, linear graphs, bar graphs and pie charts. Preferably the user is also able to "pack" or packetize data, for example, for a certain period or periods of time. The data can then be conveniently transmitted to a physician for analysis. The present invention is also preferably capable of synchronizing multiple handheld devices on a single desktop computer.

In operation, a user is preferably capable of selecting one or more items through the desktop application for uploading to a handheld device from, for example, the food database and/or the activity database. Additionally, a user can select from a full list of items provided from the USDA database as well as from updates provided by a third party or new items entered by the user.

FIGS. 3–8 illustrate operational sequences in flowchart form for one preferred embodiment of the present invention, and are self-explanatory.

Figure 9:
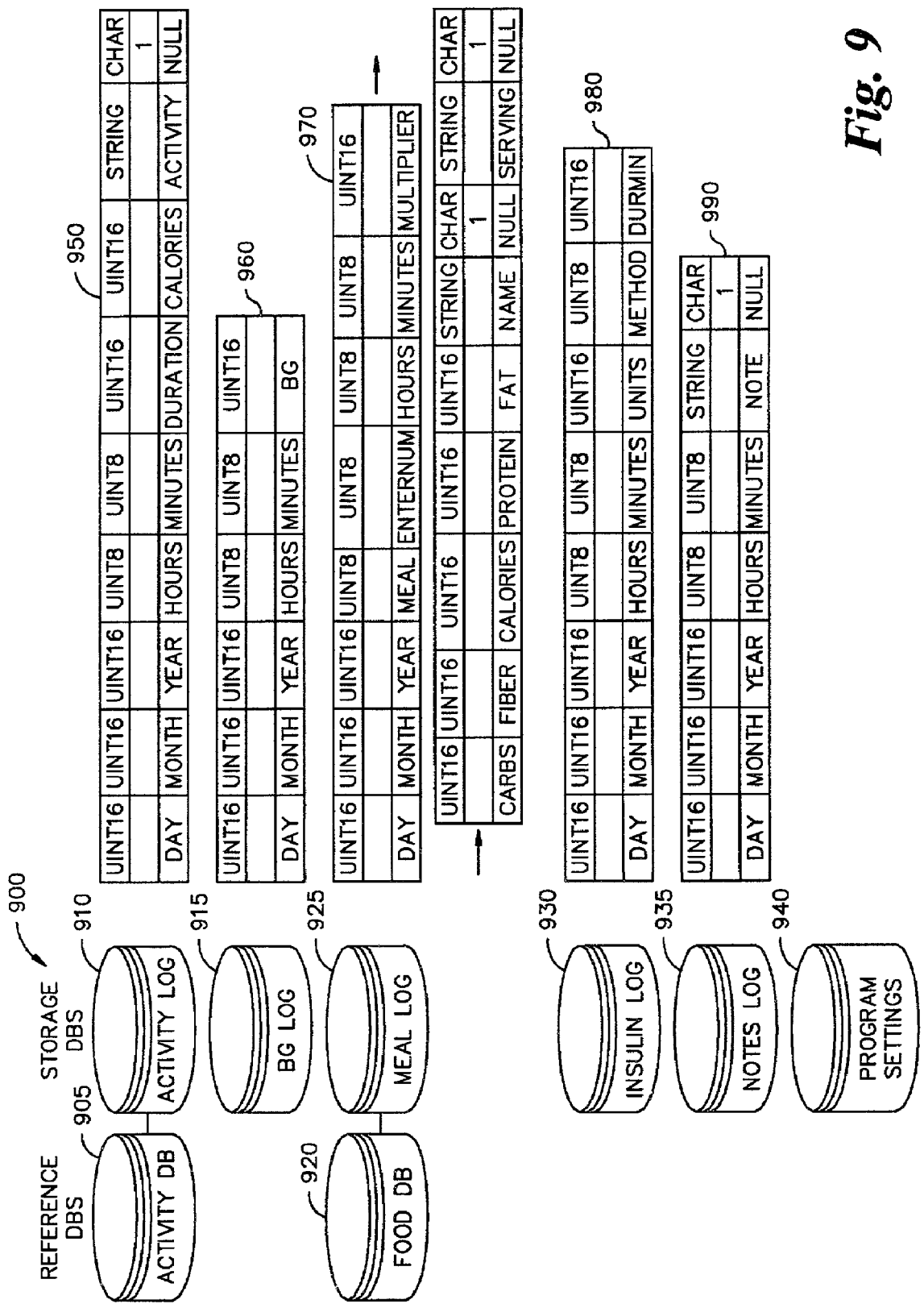
FIG. 9 shows a database system and the format of data stored in accordance with the present invention.

As discussed above, the present invention preferably incorporates the use of excerpts from the USDA food nutrition facts database on a handheld device. As shown in FIG. 9, a diabetes management system 900 according to the present invention includes an activity database 905, an activity log 910, a blood glucose log 915, a food database 920, a meal log 925, an insulin log 930, a notes log 935 and a program settings database 940. The diabetes management system 900 is preferably organized using a category system which optimizes database size and accelerates search/display sequences. The present invention preferably uses one log entry for each category. Each record 950, 960, 970, 980, 990 preferably has a corresponding date/time field (day, month, year, hours, minutes) that allows a user to enter one record independently of another and allows a physician to better understand the sequence of events when analyzing data entered by a user. By having one log for each category, the amount of data lost through unused fields is significantly reduced. Using separate tables for each log entry also provides easier review of logs at a later time by a user.

Record 950 includes activity data and is stored in activity log 910. Besides the date/time field columns, record 950 includes a field column for each of duration, calories and activity. The duration field column is the duration of an activity of the patient measured in minutes. The calories field column is the number of calories expended by the patient during exercise. The activity field column is the number of calories expended by the patient while performing the activity.

Record 960 includes blood glucose (BG) values and is stored in BG log 915. Besides the date/time field columns, record 960 includes a field column for blood glucose values recorded in milligrams per deciliter (mg/dl).

Record 970 includes meal information and is stored in meal log 925. The date/time field columns are used to uniquely define a particular meal (records grouped) in a given day. An enternum field column further defines a meal so as to allow the patient to enter the same meal in the same day and calculate it independently. This value is incremented each time a duplicate meal is created. The multiplier, carbs, fiber, calories, protein and fat field columns are unique to each food item (e.g., a piece of bread). Name and serving field columns are used to further describe food that is consumed by the patient.

Record 980 includes insulin intake information. The date/time field columns are used to uniquely define a particular meal (records grouped) in a given day. Besides the date/time field columns, record 980 includes a field column for units, method and durmin. The field column for units represents the units of insulin that the patient intakes. The method field column represents the method of insulin infusion, such as injection, bolus or extended bolus. When an extended bolus is used by the patient, the field column durmin represents the duration of the extended bolus in minutes.

Record 990 allows the patient to store notes for future review. Since records 950, 960, 970, 980, 990 are individual records containing multiple fields, the storage space required is minimized.

PDA 105 accepts data entries provided by a diabetes patient and stores them in the activity BG, meal, insulin and notes logs, as is appropriate. The PDA 105 stores and uses dosage information provided by the patient. The PDA 105 computes the total number of carbohydrates in a meal based on meal items selected by the patient. The PDA 105 also is capable of computing the necessary amount of insulin needed to compensate for hyperglycemia and the amount of carbohydrates needed to compensate for hypoglycemia. The PDA 105 is able to import and export data to a compressed and encrypted file.

The present invention also preferably includes built-in search capabilities for the food and activity databases. The search capabilities preferably include a full string search feature which allows a uses to find an item in a database as easily as entering a sequence of characters that the user is looking for. For example, when searching for "burger", items like "cheeseburger", "hamburger", "lettuce and tomato burger" will show up in a search result window.

The present invention also preferably includes additional features which provide easy database browsing, including a category search feature. By using this feature together with intuitive names for categories, the user can go through a category list and find desired items.

The present invention preferably stores complete meal information for each meal entry, including the names of foods, serving sizes, carbohydrates, calories, fiber, fat and proteins. This allows a user to better understand the complexity of the carbohydrates contained in a meal. The present invention preferably uses the complete meal information to compensate for proteins, fat, and fiber when recommending an insulin dose for a particular meal.

The present invention preferably also recommends corrective actions based on user entries. For example, if a user enters a blood glucose value that is outside his/her target range, an insulin dose is recommended which compensates for hyperglycemia or the amount of carbohydrates needed to compensate for hyperglycemia, based on corrective ratios entered by the user in a user profile. The present invention preferably also recommends corrective actions for activity, high protein meals, or the content of fiber or fat in a certain meal.

The present invention preferably also provides a user interface having large buttons and easy-to-follow names providing an easy to use interface. Point-and-click navigation capability is preferably incorporated, to allow a user to use the system without requiring the use of complicated data entry sequences or "Graffiti™" signs. Large buttons and fonts facilitate the use of the invention by users, since users suffering from diabetes commonly have vision problems.

The desktop application of the present invention is preferably designed to store information for multiple users using one or more databases. Preferably, an unlimited number of users can be created allowing each user to download information from a handheld device or from an insulin pump to separate locations in the desktop application database. Each set of data can then be processed and graphed independently, or can be exported (individually or as a whole) to other applications for display and analysis. The present invention preferably does not rely on other runtime environments.

Figure 10:
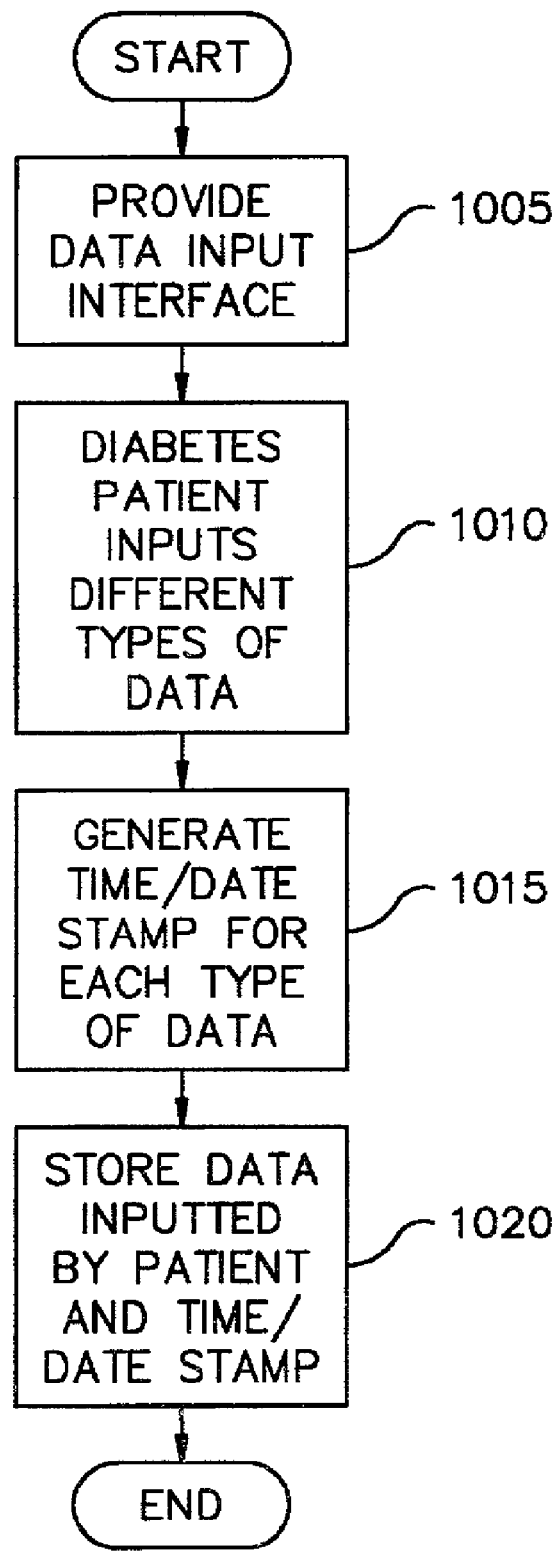
FIG. 10 shows a flow chart of providing a data input interface and storing different types of data along with a time/date stamp in accordance with the present invention.

FIG. 10 shows a flow chart illustrating how data is processed in accordance with the present invention. In step 1005, a data input interface is provided which allows a diabetes patient to input different types of data (step 1010) used to calculate at least one of insulin and carbohydrate intake recommendations for the patient. The types of inputted data include (i) activity data associated with the physical activity of the patient, (ii) blood glucose data associated with the blood glucose level of the patient, (iii) meal intake data associated with the food intake of the patient, and (iv) insulin intake data associated with the insulin intake of the patient. In step 1015, a time/date stamp is individually generated for each type of data inputted by the patient. In step 1020, the data inputted by the patient and the respective time/date stamp are stored in a database, whereby an authorized user such as the doctor of the patient may access the database to review the data entered by the patient, according to the time/date stamps.

An external food database may be accessed to calculate at least one of insulin and carbohydrate intake recommendations for the patient. The food database may provide extended search capabilities. The external food database may include at least part of the USDA food database. The external food database may include foods offered from at least one national or regional chain restaurant.

The meal intake data may be based on foods entered by the patient. The meal intake data may be based on the total nutritional content of a meal. The meal intake data may be inputted by the patient choosing one or more food items from the external food database. A portion size may be inputted which corresponds to the amount of food ingested by the patient. The blood glucose data may be received from a blood glucose meter which monitors the blood of the patient. The insulin intake data may be received from an insulin pump which distributes insulin intake into the blood of the patient. Insulin intake recommendations may be based on the food intake data. The food intake data may include at least one of carbohydrate intake data, fat intake data and protein intake data. Multiple insulin to carbohydrate compensation ratios may be stored based on a time and/or meal type deemed appropriate for the patient. The activity data may include calories burned by the patient during an activity. The carbohydrate intake recommendations may be based on the activity data.

The present invention may be implemented with any combination of hardware and software. If implemented as a computer-implemented apparatus, the present invention is implemented by using means for performing all of the steps and functions described above.

The present invention can also include an article of manufacture (e.g., one or more computer program products), having, for instance, computer user media. The media has embodied therein, for instance, computer readable code means for providing and facilitating the mechanisms for the present invention. The article of manufacture can be included as part of a computer system or sold separately.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

What is claimed is:

1. A computer-implemented method on a computer readable medium for managing the blood glucose level of a diabetes patient, the method comprising:
   providing the patient with a data input interface with which the patient performs at least three of the following:
   i. entering activity data characterizing a physical activity of the patient into a record in an activity log, whereupon an individual time/date stamp is generated and stored with the activity data in the record in the activity log;
   ii. entering blood glucose data characterizing blood glucose of the patient into a record in a blood glucose log, whereupon an individual time/date stamp is generated and stored with the blood glucose data in the record in the blood glucose log;
   iii. entering meal intake data characterizing food intake of the patient into a record in a meal log, whereupon an individual time/date stamp is generated and stored with the meal intake data in the record in the meal log;
   iv. entering insulin intake data characterizing insulin intake of a patient into a record in an insulin log, whereupon an individual time/date stamp is generated and stored with the insulin intake data in the record in the insulin log;
   obtaining data on amounts of calories burned in the activity of the patient;
   obtaining nutrition data based on food intake of the patient; and
   calculating insulin and carbohydrate intake recommendations for the patient based on the data entered in said records.

2. The method of claim 1 wherein the entering of blood glucose data comprises receiving data from a blood glucose meter which measures the blood glucose of the patient.

3. The method of claim 1 wherein entering of insulin intake data comprises receiving data from an insulin pump which delivers insulin to the patient.

4. The method of claim 1, further comprising at least one of:
   i) obtaining at least a portion of the data relating to activity of the patient is obtained from an activity database; and
   ii) obtaining at least a portion of the nutrition data is obtained from a nutrition database,
   wherein the calculating of insulin and carbohydrate intake recommendations for the patient is based at least in part on the data obtained from the activity database and/or the nutrition database.

5. A diabetes management system an a computer readable medium comprising at least three of:
   i) an activity log adapted to store activity data associated with activity of a patent and an activity database adapted to store data on amounts of calories burned during various activities, wherein first data is transferred between the activity database and the activity log;

ii) a meal log adapted to store meal intake data associated with food intake of a patient and a food database adapted to store nutrition facts on various foods, wherein second data is transferred between the food database and the meat log;

iii) a blood glucose log adapted to store data associated with a blood glucose level of a patient;

iv) an insulin log adapted to store insulin intake data associated with insulin intake of a patient; and v) a notes log adapted to store notes provided by a patient, the activity database and food database being independent from one another if both are present, wherein each of said logs has at least one record, each record including a date/time field;

wherein each of said activity log records, said blood glucose log records, said meal log records, said insulin log records and said notes log records are stored independently from one another in respective ones of said logs, and wherein i) first data is transferred between the activity database and the activity log and ii) second data is transferred between the food database and the meal log, for calculation of:

a) the insulin intake recommendations for the patient and/or b) the carbohydrate intake recommendations for the patient.

6. The system of claim 5, wherein said system is adapted to retrieve an individual record based on a time and date stored in the date/time field of the individual record.

7. The diabetes management system of claim 5, further comprising:

at least one portable electronic device comprising:

a processor, the processor in communication with at least three of: the activity log, the blood glucose log, the meal log, and the insulin log, and a data input interface, the data input interface adapted for inputting at least three types of data into the processor to calculate insulin and carbohydrate intake recommendations for the patient, the at least three types of data selected from among:

i) activity data characterizing the activity output of the patient, ii) blood glucose data characterizing the blood glucose level of the patient, iii) meal intake data characterizing the food intake of the patient, and iv) insulin intake data characterizing the insulin intake of the patient, wherein the inputted data are each stored in respective ones of said records in the activity log, the blood glucose log, the meal log, and the insulin log.

8. The diabetes management system of claim 7, wherein an individual time/date stamp is generated for each record and stored in the corresponding date/time field.

9. A diabetes management system on a computer readable medium comprising:

an activity database adapted to store data on amounts of calories burned during various activities;

a food database adapted to store nutrition facts on various foods, the activity database and food database being independent from one another;

an activity log adapted to store activity data associated with activity of a patent;

a blood glucose log adapted to store data associated with a blood glucose level of the patient;

a meal log adapted to store meal intake data associated with food intake of the patient;

an insulin log adapted to store insulin intake data associated with insulin intake of the patient; and a notes log adapted to store notes associated with the patient, wherein each of said logs has at least one record, each record including a date/time field, wherein each of said activity log records, said blood glucose log records, said meal log records, said insulin log records and said notes log records are stored independently from one another in respective ones of said logs, and wherein insulin and/or carbohydrate intake recommendations for the patient are determined based on the data entered in said records.

10. A diabetes management system comprising:

an activity database adapted to store data on a computer readable medium on amounts of calories burned during various activities;

a blood glucose lag adapted to store data associated with a blood glucose level of the patient;

a meal log adapted to store meal intake data associated with food intake of the patient; and an insulin log adapted to store insulin intake data associated with insulin intake of the patient;

wherein each of said logs has at least one record, each record including a date/time field, wherein each of said blood glucose log records, said meal log records, and said insulin log records are stored independently from one another in respective ones of said logs, and wherein insulin and/or carbohydrate intake recommendations for the patient are determined based on the data entered in said records.

11. The diabetes management system of claim 10 further comprising a blood glucose meter, wherein the data associated with the blood glucose level of the patient stored in the blood glucose log is based on data received from the blood glucose meter, which measures the blood glucose level of the patient.

12. The diabetes management system of claim 10 further comprising an insulin pump, wherein the insulin intake data is received from the insulin pump which delivers insulin to the patient.

13. The diabetes management system of claim 10 further comprising a desktop application running on a desktop computer that synchronizes data logs contained within the portable electronic device with corresponding data logs contained in the desktop computer.

14. The diabetes management system of claim 13 wherein the desktop application is adapted to allow data from the date logs to be organized into at least two formats, including tabular listings, linear graphs, bar graphs, and pie charts, and by specific periods of time.

15. The system of claim 10, further comprising a food database adapted to store nutrition facts on various foods, the activity database and food database being independent from one another.

16. The diabetes management system of claim 15 wherein the food database includes at least one of the following:

a USDA food database, a database of favorite foods of the patient, and a database of foods offered from at least one national or regional chain restaurant.

17. The system of claim 15, wherein the meal log is adapted to receive data related to food selection of the patient from the food database.

18. The system of claim 15, wherein i) first data is transferred between the activity database and the activity log and ii) second data is transferred between the food database and the meal log, for calculation of:
  a) the insulin intake recommendations for the patient and/or
  b) the carbohydrate intake recommendations for the patient.

19. The system of claim 10, further comprising an activity log adapted to store activity data associated with activity of the patent, the activity log having at least at least one record, each of said at least one record including a date/time field, wherein said activity log records are stored independently from said blood glucose log records, said meal log records, and said insulin log records.

20. The system of claim 10, further comprising a notes log adapted to store notes associated with the patient, the notes log having at least at least one record, each of said at least one record including a date/time field, wherein said notes log records are stored independently from said activity log records, said blood glucose log records, said meal log records, and said insulin log records.

21. The system of claim 10, wherein said system is adapted to retrieve an individual record based on a time and date stored in the date/time field of the individual record.

22. The diabetes management system of claim 10 further comprising:
  at least one portable electronic device comprising:
    a processor, the processor in communication with at least three of i) the activity log, ii) the blood glucose log, iii) the meal log, and iv) the insulin log, and
    a data input interface, the data input interface adapted for inputting at least three types of data into the processor to calculate insulin and carbohydrate intake recommendations for the patient, the at least three types of data selected from the group consisting of:
      i) activity data characterizing the activity output of the patient,
      ii) blood glucose data characterizing the blood glucose level of the patient,
      iii) meal intake data characterizing the food intake of the patient, and
      iv) insulin intake data characterizing the insulin intake of the patient,
    wherein the inputted data are each stored in respective ones of said records in the activity log, the blood glucose log, the meal log, and the insulin log.

23. The diabetes management system of claim 22, wherein an individual time/date stamp is generated for each record and stored in the corresponding date/time field.

* * * * *